United States Patent [19]

Wheelock

[11] 4,055,513

[45] Oct. 25, 1977

[54] PEROVSKITE CATALYSTS AND PROCESS FOR THEIR PREPARATION

[75] Inventor: Kenneth S. Wheelock, Baton Rouge, La.

[73] Assignee: Exxon Research & Engineering Co., Linden, N.J.

[21] Appl. No.: 676,511

[22] Filed: Apr. 13, 1976

[51] Int. Cl.² .................. B01J 21/04; B01J 23/02; B01J 23/10; B01J 23/78
[52] U.S. Cl. .................. 252/462; 252/461; 252/463; 252/467; 252/471; 252/472; 252/475; 252/476
[58] Field of Search .............. 252/462, 463, 461, 467, 252/475, 476, 471, 472

[56] References Cited

U.S. PATENT DOCUMENTS

| 3,368,982 | 2/1968 | Milbourne | 252/466 J |
|---|---|---|---|
| 3,901,828 | 8/1975 | Mai et al. | 252/462 |

Primary Examiner—W. J. Shine
Attorney, Agent, or Firm—Marthe L. Gibbons

[57] ABSTRACT

A high surface area perovskite catalyst comprises a perovskite containing at least one transition metal composited with a spinel-coated metal oxide support. The catalyst is prepared by forming a surface spinel on a metal oxide and subsequently co-impregnating or co-depositing the appropriate perovskite precursor component on the spinel coated metal oxide, followed by calcination at a temperature of at least 540° C. A preferred catalyst is $LaCoO_3$ supported on a spinel-covered alumina.

22 Claims, No Drawings

PEROVSKITE CATALYSTS AND PROCESS FOR THEIR PREPARATION

BACKGROUND OF THE INVENTION

1. Field of the Invention

The present invention relates to novel perovskite catalysts, methods for their preparation and uses thereof in hydrocarbon conversion processes.

2. Description of the Prior Art

It is known that perovskites can be used as hydrocarbon conversion catalysts (see, for example, U.S. Pat. Nos. 3,595,809; 3,450,789; 3,780,126; and U.K. Pat. No. 1,352,995). The conventional method of preparing pure perovskites has been a repetition of the steps of high temperature fusion of a mixture of metal oxides and ball milling to reduce the fused mass to submicron size particles and to expose fresh unreacted oxide for the repeated fusion step. Due to the repeated high temperature treatments which induce melting and sintering, the thus prepared perovskites have relatively low surface areas, typically from about 1 to about 20 $m^2/g$ (BET).

U.S. Pat. No 3,897,367 discloses perovskite-type compounds which may be employed as catalyst in the form of coatings on suitable refractory supports.

For use as catalysts, especially for use as hydrocarbon conversion catalysts, it is desirable to obtain high surface area perovskites. Attempts to produce supported high surface area perovskite catalysts by simple impregnation techniques on alumina gel resulted in a supported spinel and not in the desired supported perovskite.

It has now been found that high surface area perovskite catalysts can be produced by the preparation methods of the present invention.

SUMMARY OF THE INVENTION

In accordance with the invention, there is provided a supported perovskite catalyst which comprises a perovskite containing at least one transition metal composited with a support comprising a metal oxide and a spinel on the surface of said metal oxide.

Furthermore, in accordance with the invention, there is also provided a process for preparing a supported perovskite catalyst which comprises (a) treating a metal oxide with at least one metal component such that the algebraic sum of the ionic charges of the metal of said metal oxide and the metal of said metal component corresponds to the algebraic sum of cations required for spinel formation; (b) calcining the treated metal oxide resulting from step (a), thereby producing a spinel on at least a portion of the surface of said treated metal oxide; (c) treating the calcined metal oxide having said surface spinel thereon, resulting from step (b), with perovskite precursor metal components, said precursor metal components comprising at least one transition metal component, (d) calcining at a temperature of at least 540° C. the perovskite precursor-treated material resulting from step (c) to convert said perovskite precursors to a perovskite and thereby produce a supported perovskite catalyst.

The term "transition metal" is intended herein to designate elements having atomic numbers ranging from 21 through 30, from 39 through 48, from 57 through 80 and from 89 through 92.

DESCRIPTION OF THE PREFERRED EMBODIMENTS

The supported perovskite catalyst of the present invention comprises a perovskite comprising at least one transition metal composited with a support comprising a metal oxide and a spinel on the surface of the metal oxide. The term "perovskite" is intended herein to designate metal oxides having the ideal and non-ideal perovskite-type crystalline structure. The ideal perovskite crystalline structure is defined by the empirical formula $ABO_3$ in which A and B are cations of two different metals and in which the A cation is coordinated to twelve oxygen atoms while the B cation occupies octahedral sites and is coordinated to six oxygen atoms. The ideal perovskite structure is cubic, however, few compounds have this ideal structure. The term "perovskite" structure draws its name from the mineral perovskite ($CaTiO_3$) which was first thought to have a cubic structure that has now been determined to be orthorhombic. For example, the compound $LaMnO_3$ has the ideal structure while some complex oxides, such as $La_{0.7}Sr_{0.3}MnO_3$ which exhibit a variety of other structures are still classed as perovskite-type structures. A more complete description of the perovskite-type structure is found in *Structural Inorganic Chemistry*, A. F. Wells, 3rd Edition, Oxford, the Clarendon Press, 1962, pages 494 to 499. In general the algebraic sum of the ionic charges of the two or more metals (cations) of the perovskite equals plus six.

The term "spinel" is intended herein to designate a binary oxide having the normal spinel structure or the inverse spinel structure. The normal spinel may be represented by the formula $MY_2O_4$ wherein M and Y are cations of different metals. The inverse spinel may be represented by the formula $Y(XY)O_4$ wherein Y and X are cations of different metals. The sum of the cationic charges of the spinel equals 8. The crystallographic structures of the normal and inverse spinels are given in the above mentioned A. F. Wells, *Structural Inorganic Chemistry*, pp. 487–488.

Suitable metal oxide components of the catalysts include $Al_2O_3$; MgO; $TiO_2$; $Zr_2O$; $Hf_2O$; $WO_3$ and mixtures thereof.

The supported perovskite catalysts of the invention are prepared by the following steps: a metal oxide is treated with at least one metal component such that the sum of the ionic charges of the metal of the metal oxide and of the metal of the metal component (or metals of the metal components) satisfy the requirement for spinel formation, that is, that the sum equals 8 and that the ionic radii of the metals satisfy the requirements for spinel formation of the normal spinel type or of the inverse spinel type structure. The metal oxide utilized may be a porous metal oxide or a porous metal oxide gel. The surface area of the initially utilized metal oxide will generally range from about 50 $m^2/g$ to about 250 $m^2/g$. Suitable metal oxides include $Al_2O_3$; MgO; $TiO_2$; $ZrO_2$; $HfO_2$; $WO_3$ and mixtures thereof.

Suitable metal components for the treatment of the metal oxide are compounds having cations that will complement the cation of the metal oxide to satisfy the rule of spinel formation. By way of example, suitable metal components include metals, metal oxides, metal hydroxides, metal salts of Mg, Fe Co, Ni, Mn, Zn, Ti, Sn, Cu, Cr, etc.

The treatment of the metal oxide is generally carried out by utilizing a solution of the desired metal component to impregnate or deposit the metal component on the metal oxide. The treated metal oxide is subsequently calcined at a temperature ranging from about 500° to about 1000° C. Calcination of the treated metal oxide produces a surface spinel on at least a portion of the metal oxide. If desired, the metal component can be used in a sufficient amount in the treatment to cover all of the surface of the metal oxide. The metal oxide having the surface spinel thereon is subsequently treated with perovskite precursor metal components. This treatment may be effected by co-impregnation or co-deposition of the appropriate perovskite precursor metal components on the metal oxide having the surface spinel. The perovskite precursors are components which contain cations, the sum of which will equal plus six and which cations have ratios of ionic radii that satisfy the requirements for perovskite formation. The requirements for perovskite formation are given in *Structure, Properties and Preparation of Perovskite-type Compounds* by Francis S. Galasso, Pergamon Press, Oxford, 1969. Suitable perovskite precursor components include metals, metal oxides, metal hydroxides, metal salts and mixtures thereof of metals having valences ranging from 1 to 5, such as silver, niobium, cesium, potassium, rubidium, barium, iron, lead, strontium, lanthanum, cobalt, aluminum, lead and the like, and mixtures thereof. The perovskite precursor components used to prepare the catalysts of the present invention must comprise at least one transition metal component. Subsequently, the perovskite precursor treated material is calcined at a temperature of at least 540° C., generally at a temperature ranging from about 540° C. to about 1040° C., for example, at about 600° C. to produce a perovskite on the spinel-coated metal oxide. The final supported perovskite catalysts will have a surface area of at least 65 m²/g, preferably a surface area ranging from about 65 m²/g to about 250 m²/g. Additional catalytic active metal components may be composited with the supported perovskite catalysts.

The novel catalysts of the invention can be used in a number of hydrocarbon conversion processes and hydrocarbon treating processes such as cracking, reforming, hydrogenation, oxidation, dehydrocyclation, isomerization, hydrocracking, hydrodesulfurization, denitrogenation, demetallization, etc.

The following examples are presented to illustrate the invention.

EXAMPLE 1

A gamma alumina gel having a surface area of about 185 m²/g (50 g thereof) was impregnated with $Mg(NO_3)_{2(-g)}$. The impregnated material was calcined at 540° C. thereby producing a surface coating of $MgAl_2O_4$ (a spinel) on the alumina. The resulting material was re-impregnated with an equally molar solution of $La(NO_3)_3 \cdot 6H_2O$ and $Co(NO_3)_2 \cdot 6H_2O$ and subsequently calcined at the temperature of 600° C. The calcined material had a surface coating of the perovskite, $LaCoO_3$, as identified by ESCA (Electron Spectrometry for Chemical Analysis).

The color of the preparation was black. When the same gamma alumina was treated directly with the same equimolar solution of $La(NO_3)_3 \cdot 6H_2O$ and $Co(NO_3)_2 \cdot 6H_2O$ and subsequently calcined at 600° C., the color of the preparation was 50% blue and 50% black. The blue color was attributed to the formation of $CoAl_2O_4$ (as spinel) and ESCA identification was negative for the perovskite $LaCoO_3$. These results indicate the necessity of first forming a spinel on the metal oxide support prior to treating it with a perovskite precursor to prepare a supported perovskite.

EXAMPLE 2

The supported $LaCoO_3$ perovskite catalyst prepared by the method of the invention given in Example 1 was tested as a hydrocarbon conversion catalyst. The tests were conducted as follows: hydrogen carrier gas is bubbled through a gas scrubbing tower containing an appropriate pure hydrogen feed, entraining vapors of the feed. This gas stream then contacted the catalyst contained in a reactor maintained at the desired temperature in a sandbath, wherein conversion of the feed was effected. Reaction products were determined by sampling the effluent downstream of the reactor and analyzing and identifying the product mixture by means of gas chromatography. The operation was carried out at 0 psig total pressure and hydrocarbon space velocities varying from 0.5 to 3.0 W/Hr./W. The temperature of operation varied from 150° C. to 500° C.

The results of the tests are summarized in Table I.

TABLE I
HYDROCARBON CONVERSION WITH SUPPORTED $LaCoO_3$
Product Analyses (Gas Chromatograhic Area %)

| Component | Cyclohexane Conversion | n-Heptane Conversion | Cumene Conversion | Methylcyclopentane Conversion |
|---|---|---|---|---|
| 2,3-DMB/2-MP | 5.6 | 0.0 | 0.0 | 0.0 |
| n-Hexane | 7.0 | 1.8 | 3.6 | 2.2 |
| Methylcyclopentane | 0.0 | 64.0 | 15.8 | 60.0 |
| Cyclohexane | 66.0 | 28.4 | 23.4 | 32.8 |
| Heptanes | 21.5 | 0.0 | 12.4 | 1.2 |
| Benzene | 0.0 | 3.1 | 1.8 | 1.9 |
| Toluene | 0.0 | 0.0 | 0.1 | 0.0 |
| Cumene | 0.0 | 0.0 | 0.0 | 0.0 |

EXAMPLE 3

A supported $LaCoO_3$ pervoskite was prepared as follows. Fifty grams of spinel treated alumina were weighed. The spinel treated alumina was obtained by treating alumina with $Mg(NO_3)_2$ and calcining it to form a monolayer of MgO which formed $MgAl_2O_4$. A solution of 20.16 g $La(NO_3)_3 \cdot 6H_2O$ and 11.62 g $Co(CH_3CO_2)_2 \cdot 4H_2O$ was made by dissolving in 25 cc distilled water by heating and stirring. When the materials were dissolved, the volume of solution was brought up to 50 cc, stirred and then the solution was added to the support by the method of incipient wetness. The solids were predried for 2 hours at 130° C. and calcined at 1000° C. to yield a supported $LaCoO_3$ perovskite.

EXAMPLE 4

A supported $LaCrO_3$ was prepared utilizing the identical procedure used in Example 3 and using 50.00 g spinel treated alumina (the same as the one used in Example 3), 20.20 g $La(NO_3)_3 \cdot 6H_2O$ and 18.63 g Cr(NO$_3$)$_3$. 9H$_2$O. The solids were predried one hour at 130° C. The sample was split and one part was fired at 600° C. and the remainder at 1000° C. to yield a supported LaCrO$_3$ perovskite.

EXAMPLE 5

A supported SrSnO$_3$ was prepared as follows. Fifty grams of the same spinel treated alumina (as the one utilized in Example 3) were weighed. 24.28 g of Sr(OH)$_2$. 8H$_2$O and 20.60 g SnCl$_2$ were dissolved in 25 cc of concentrated HCl with heating and stirring. When the materials were dissolved, the volume of solution was brought up to 50 cc by the addition of concentrated HCl. The resulting solution was added to the support by the method of incipient wetness. The solids were predried at ambient conditions and then calcined at 800° C. to yield a supported SrSnO$_3$.

EXAMPLE 6

The supported perovskites prepared in accordance with Examples 3 to 5 were tested for catalytic activity. The results of these tests are summarized in Tables II to IV.

As can be seen from Table IV, SrSnO$_3$ on spinel-treated alumina, that is, a perovskite which did not contain at least one transition metal, did not have any significant catalytic activity according to the comparative tests utilized.

EXAMPLE 7

A number of supported perovskites were tested for their activity as catalyst for various hydrocarbon conversion reactions. Results of these tests are summarized in Tables VI to XXI.

The experimental procedures used in experiments reported in Tables VI to XXI were as follows.

A controlled flow of carrier gas, either hydrogen or helium, is admitted to a gas scrubbing tower containing the appropriate pure hydrocarbon. The flowing gas entrains vapors of the hydrocarbon and serves as the feed supply to the reactor. Knowing the temperature of the hydrocarbon in the gas tower determines the vapor pressure of the hydrocarbon. A knowledge of the vapor pressure of the hydrocarbon, the absolute flow of the carrier gas under standard conditions, and the barometric pressure enables the hydrocarbon feed rate to be calculated.

The gas exiting the gas scrubbing tower is a mixture of the hydrocarbon vapor and the carrier gas. This gas mixture is transported through heated lines to a reactor containing the catalyst to be tested wherein it contacts the catalyst and then exits the reactor. The product gas mixture is usually a complicated mixture of various hydrocarbons as well as the carrier gas and is transported from the reactor to a sampling point through heated lines. Heated lines are necessary to prevent condensation.

The product is sampled via a port protected with a septum. A syringe is injected through the septum and the sample withdrawn. The sample is injected into a gas chromatograph and analyzed as to its components and their relative percentages. Once feed is introduced to the catalyst, samples are taken approximately every 60 minutes over a 5 hour test period.

TABLE II

LaCrO$_3$ ON SPINEL TREATED ALUMINA (CALCINED AT 600° C), S.A.=133 M$^2$/G.

| Reaction Activity | Cyclohexane Dehydrogenation to Make Benzene | | Methylcyclopentane Reforming to Make Benzene | | N-Hexane Isomerization to Make Hexane Isomers | |
|---|---|---|---|---|---|---|
| | Initial | Lined-Out | Initial | Lined-Out | Initial | Lined-Out |
| At Time (Min.) | 5 | 297 | 5 | 239 | 7 | 229 |
| Wt. % Conversion | 29 | 18 | 5 | 10 | 5 | 4 |
| % Selectivity to Desired Product | 13 | 97 | 18 | 13 | 69 | 85 |
| Temp. ° C | | 495 | | 495 | | 150 |
| W/Hr/W | | 0.5 | | 1.5 | | 1.5 |

TABLE III

LaCrO$_3$ ON SPINEL TREATED ALUMINA (CALCINED AT 1000° C), S.A.=94 M$^2$/G

| Reaction Activity | Cyclohexane Dehydrogenation to Make Benzene | | Methylcyclopentane Reforming to Make Benzene | | N-Hexane Isomerization to Make Hexane Isomers | |
|---|---|---|---|---|---|---|
| | Initial | Lined-Out | Initial | Lined-Out | Initial | Lined-Out |
| at Time (Min.) | 5 | 300 | 5 | 186 | 5 | 271 |
| Wt % Conversion | 31 | 14 | 34 | 7 | 4 | 6 |
| % Selectivity to Desired Product | 12 | 93 | 6 | 14 | 77 | 87 |
| Temp. ° C | | 495 | | 495 | | 150 |
| W/Hr/W | | 0.5 | | 1.5 | | 1.5 |

TABLE IV

SrSnO$_3$ ON SPINEL TREATED ALUMINA (CALCINED AT 800° C), S.A. = 106 M$^2$/G

| Reaction Activity at | Cyclohexane Dehydrogenation to Make Benzene | | Methylcyclopentane Reforming to Make Benzene | | N-Hexane Isomerization to Make Hexane Isomers | |
|---|---|---|---|---|---|---|
| | Initial | Lined-Out | Initial | Lined-Out | Initial | Lined-Out |
| Time (Min) | 5 | 202 | 5 | 137 | 5 | 147 |
| Wt. % Conversion | 1 | 1 | 38 | 2 | 3 | 3 |
| % Selectivity to Desired Product | 0 | 0 | 4 | 36 | 87 | 94 |
| Temp. ° C | | 495 | | 495 | | 150 |
| W/Hr/W | | 0.5 | | 1.5 | | 1.5 |

The unit is operated at atmospheric pressure (Opsig). Although this does not duplicate many commercial processes which are usually operated under pressure, this pressure is convenient for a laboratory determination of catalyst activity and low pressure is a more severe condition for catalyst testing than high pressure; high pressures of hydrogen being used commercially to prevent catalyst deactivation.

The catalysts tested are given a pretreatment with hydrogen for two hours before admitting feed to the system.

The experimental conditions utilized in the tests reported in Tables VI to XXI are summarized in Table V.

TABLE V

| Feedstock (Pure) | Temp. °C. | Carrier Gas | W/Hr/W* |
|---|---|---|---|
| Cyclohexane | 494 | $H_2$ | 1 |
| Methyl cyclopentane | 494 | $H_2$ | 3 |
| n-heptane | 494 | $H_2$ | 1 |
| n-hexane | 150 | He | 3 |
| Benzene | 150 | $H_2$ | 2 |

*These values vary somewhat depending on the bulk density of the catalyst charged. Catalyst charges are 1 cc in all cases of 20–40 mesh material.

TABLE VI
CYCLOHEXANE CONVERSION TO BENZENE

Catalyzed by $LaCrO_3$ on Spinel Treated Alumina (calcined at 1000° C)
Conditions: 495° C, 0 psig

| Time (Min) | 5 | 175 | 215 | 255 | 300 |
|---|---|---|---|---|---|
| Product (Wt. %) | | | | | |
| 2,3-dimethylbutane and 2-methylpentane | 26.76 | 0.07 | 0 | 0.03 | 0.04 |
| Methylcyclopentane | 0 | 0.12 | 0.16 | 0.10 | 0.10 |
| Cyclohexane (feed) | 69.17 | 84.86 | 84.76 | 85.28 | 85.54 |
| Benzene | 3.65 | 14.50 | 14.02 | 12.99 | 13.50 |
| Other | 0.42 | 0.45 | 1.06 | 1.60 | 0.82 |
| Wt. % Conversion | 30.83 | 15.14 | 15.24 | 14.72 | 14.46 |
| Selectivity to benzene | 11.8 | 95.8 | 92.0 | 88.2 | 93.4 |

TABLE VII
CYCLOHEXANE CONVERSION TO BENZENE

Catalyzed by $LaCrO_3$ on Spinel Treated Alumina (Calcined at 600° C)
Conditions: 494° C, 0 psig

| Time (Min.) | 5 | 170 | 212 | 256 | 297 |
|---|---|---|---|---|---|
| Product (Wt. %) | | | | | |
| 2,3-dimethyl butane and 2 methylpentane | 24.90 | 0 | 0.03 | 0.05 | 0 |
| Methylcyclopentane | 0 | 0.12 | 0.14 | 0.13 | 0.09 |
| Cyclohexane (feed) | 70.66 | 84.34 | 85.45 | 83.59 | 82.17 |
| Benzene | 3.73 | 15.37 | 14.02 | 15.28 | 17.26 |
| Other | 0.71 | 0.17 | 0.36 | 0.95 | 0.48 |
| Wt. % Conversion | 29.34 | 15.66 | 14.55 | 16.41 | 17.83 |
| Selectivity to Benzene | 12.7 | 98.1 | 96.4 | 93.1 | 96.8 |

TABLE VIII
CYCLOHEXANE CONVERSION TO BENZENE

Catalyzed by $SrSnO_3$ on Spinel Treated Alumina
Conditions: 494° C, 0 psig

| Time (Min.) | 5 | 102 | 202 |
|---|---|---|---|
| Product (Wt. %) | | | |
| Cyclohexane | 99.21 | 99.14 | 99.12 |
| Benzene | 0 | 0 | 0 |
| Other | 0.79 | 0.86 | 0.88 |
| Wt % Conversion | 0.79 | 0.86 | 0.88 |
| % Selectivity to Benzene | 0.0 | 0.0 | 0.0 |

TABLE IX
METHYLCYCLOPENTANE CONVERSION TO HEXANE ISOMERS

Catalyzed by $CaThO_3$ on Spinel Treated Alumina
Conditions: 494° C, 0 psig

| Time (Min.) | 5 | 86 | 127 | 183 | 248 |
|---|---|---|---|---|---|
| Product (Wt. %) | | | | | |

TABLE IX-continued
METHYLCYCLOPENTANE CONVERSION TO HEXANE ISOMERS

Catalyzed by $CaThO_3$ on Spinel Treated Alumina
Conditions: 494° C, 0 psig

| Time (Min.) | 5 | 86 | 127 | 183 | 248 |
|---|---|---|---|---|---|
| 2,3-dimethylbutane and 2-methylpentane | 32.97 | 8.25 | 0 | 0 | 0 |
| 3-methylpentane | 2.18 | 2.80 | 0 | 0 | 0 |
| n-hexane | 1.99 | 1.99 | 0 | 0 | 0.11 |
| Methylcyclopentane (feed) | 60.62 | 84.73 | 96.96 | 96.84 | 97.45 |
| Cyclohexane | 1.19 | 1.39 | 1.41 | 1.38 | 1.12 |
| Other | 1.05 | 1.64 | 1.63 | 1.78 | 1.32 |
| Wt. % Conversion | 39.38 | 15.27 | 3.04 | 3.16 | 2.55 |
| % Selectivity to $C_6$ Isomers | 97.3 | 89.3 | 46.4 | 43.7 | 48.2 |

TABLE X
METHYLCYCLOPENTANE CONVERSION TO BENZENE

Catalyzed by $LaCrO_3$ on Spinel Treated Alumina (Calcined at 600° C)
Conditions: 494° C, 0 psig

| Time (Min.) | 5 | 51 | 132 | 173 | 238 | 282 |
|---|---|---|---|---|---|---|
| Product (wt.%) | | | | | | |
| 2,3-dimethylbutane and 2-methylpentane | 0 | 1.02 | 0.74 | 1.19 | 0.79 | 0.51 |
| Methyl cyclopentane | 95.39 | 92.43 | 89.95 | 90.34 | 90.47 | 92.54 |
| Cyclohexane | 2.30 | 3.93 | 4.54 | 4.62 | 4.54 | 4.48 |
| Benzene | 0.83 | 0.92 | 1.14 | 0.99 | 1.28 | 0.89 |
| Other | 1.48 | 4.10 | 3.63 | 2.86 | 2.92 | 1.58 |
| Wt. % Conversion | 4.61 | 7.57 | 10.05 | 9.66 | 9.53 | 7.46 |
| % Selectivity to Benzene | 18.0 | 12.2 | 11.3 | 10.2 | 13.4 | 11.9 |

TABLE XI
METHYLCYCLOPENTANE CONVERSION TO BENZENE

Catalyzed by $LaCrO_3$ on Spinel Treated Alumina (Calcined at 1000°)
Conditions: 495° C, 0 psig

| Time (Min.) | 5 | 90 | 139 | 186 |
|---|---|---|---|---|
| Product (Wt. %) | | | | |
| 2,3-dimethylbutane and 2-methylpentane | 28.32 | 0.52 | 0.51 | 0.39 |
| Methyl cyclopentane | 65.76 | 85.67 | 92.48 | 93.32 |
| Cyclohexane | 2.57 | 4.27 | 3.86 | 3.55 |
| Benzene | 2.03 | 1.36 | 1.30 | 0.90 |
| Other | 1.32 | 8.18 | 1.85 | 1.84 |
| Wt. % Conversion | 34.24 | 14.33 | 7.52 | 6.68 |
| % Selectivity to Benzene | 5.9 | 9.5 | 17.3 | 13.5 |

TABLE XII
n-HEPTANE CONVERSION TO HEXANE ISOMERS

Catalyzed by $LaCrO_3$ on Spinel Treated Alumina (Calcined at 600° C)
Conditions: 494° C, 0 psig

| Time (Min.) | 5 | 46 | 93 | 139 | 288 |
|---|---|---|---|---|---|
| Product (Wt. %) | | | | | |
| 2,3-dimethylbutane and 2-methylpentane | 61.20 | 40.59 | 0 | 0.07 | 0.10 |
| Methylcyclopentane | 9.16 | 7.29 | 8.43 | 3.63 | 4.43 |
| Cyclohexane | 1.87 | 1.80 | 2.38 | 0.41 | 0.64 |
| n-heptane (feed) | 27.07 | 48.16 | 82.52 | 91.70 | 89.10 |
| Other | 0.70 | 2.16 | 6.67 | 4.19 | 5.73 |
| Wt. % Conversion | 72.93 | 51.84 | 17.48 | 8.30 | 10.90 |
| % Selectivity to $C_6$ Isomers | 99.0 | 95.8 | 61.8 | 49.5 | 47.4 |

TABLE XIII
n-HEPTANE CONVERSION TO HEXANE ISOMERS

Catalyzed by $CaThO_3$ on Spinel Treated Alumina
Conditions: 494° C, 0 psig

| Time (Min.) | 6 | 137 | 182 | 289 | 298 |
|---|---|---|---|---|---|
| Product (Wt. %) | | | | | |
| 2,3-dimethylbutane and 2-methylpentane | 74.03 | 20.82 | 0 | 0 | 0 |
| Methylcyclopentane | 3.64 | 5.76 | 0 | 0.64 | 0.67 |
| Cyclohexane | 2.03 | 2.12 | 0.29 | 0 | 0.22 |
| n-hexane | 0 | 0 | 0 | 0.23 | 0.23 |
| n-heptane (feed) | 20.21 | 69.66 | 97.95 | 97.63 | 98.57 |
| Other | 0.09 | 1.64 | 1.76 | 1.50 | 0.31 |

TABLE XIII-continued n-HEPTANE CONVERSION TO HEXANE ISOMERS

Catalyzed by CaThO3 on Spinel Treated Alumina
Conditions: 494° C, 0 psig

| Time (Min.) | 6 | 137 | 182 | 289 | 298 |
|---|---|---|---|---|---|
| Wt. % Conversion | 79.79 | 30.34 | 2.05 | 2.37 | 1.43 |
| % Selectivity to C6 Isomers | 99.9 | 94.6 | 14.1 | 36.7 | 78.3 |

TABLE XIV n-HEPTANE CONVERSION TO HEXANE ISOMERS

Catalyzed by AgNbO3 on Spinel Treated Alumina
Conditions: 494° C, 0 psig

| Time (Min.) | 6 | 82 | 132 | 178 | 233 |
|---|---|---|---|---|---|
| Product (Wt. %) | | | | | |
| n-hexane | 0.40 | 0 | 0.26 | 0.19 | 0.17 |
| Methylcyclopentane | 14.66 | 0 | 5.47 | 4.09 | 3.40 |
| Cyclohexane | 2.31 | 0 | 0.46 | 0 | 0.38 |
| n-heptane (feed) | 75.20 | 85.04 | 90.25 | 91.30 | 93.87 |
| Methylcyclohexane | 2.00 | 1.57 | 0.37 | 0.80 | 0 |
| Toluene | 1.20 | 0 | 0.17 | 0 | 0 |
| Other | 4.23 | 13.39 | 3.02 | 3.62 | 2.18 |
| Wt. % conversion | 24.80 | 14.96 | 9.75 | 8.70 | 6.13 |
| Selectivity to C6 | 70.0 | 0 | 63.5 | 49.2 | 64.4 |
| Selectivity to toluene | 4.8 | 0 | 1.7 | 0 | 0 |

TABLE XV n-HEXANE ISOMERIZATION

Catalyzed by AgNbO3 on Spinel Treated Alumina
(S.A. = m²/g)
Conditions: 148° C, 0 psig

| Time (Min.) | 5 | 85 | 127 | 168 | 213 | Avg. |
|---|---|---|---|---|---|---|
| Product (Wt. %) | | | | | | |
| 2,3-dimethylbutane and 2-methylpentane | 54.66 | 32.25 | 21.69 | 21.87 | 18.34 | |
| 3-methylpentane | 0 | 1.95 | 0 | 0 | 1.98 | |
| Methylcyclopentane | 2.64 | 3.02 | 5.08 | 4.82 | 3.00 | |
| Cyclohexane | 0 | 0 | 0 | 0 | 1.08 | |
| n-hexane (feed) | 41.71 | 61.50 | 72.30 | 71.68 | 74.89 | |
| Other | 0.99 | 1.28 | 0.93 | 1.63 | 0.71 | |
| Wt. % Conversion | 58.29 | 38.50 | 27.70 | 28.32 | 25.11 | 35.6 |
| % Selectivity to C6 Isomers | 98.3 | 96.7 | 96.6 | 94.2 | 97.2 | 96.6 |

TABLE XVI n-HEXANE ISOMERIZATION

Catalyzed by CaThO3 on Spinel Treated Alumina
(S.A. = m²/g)
Conditions: 148° C, 0 psig

| Time (Min.) | 5 | 97 | 149 | 266 | Avg. |
|---|---|---|---|---|---|
| Product (Wt. %) | | | | | |
| 2,3-dimethylbutane and 2-methylpentane | 37.84 | 8.61 | 0.43 | 0.44 | |
| 3-methylpentane | 1.74 | 1.80 | 0.45 | 0.45 | |
| Methylcyclopentane | 2.38 | 2.91 | 2.74 | 1.76 | |
| Cyclohexane | 0.84 | 0.67 | 0.63 | 0 | |
| n-hexane (feed) | 56.79 | 84.70 | 94.67 | 96.38 | |
| Wt. % Conversion | 43.21 | 15.30 | 5.33 | 3.62 | 16.9 |
| % Selectivity to C6 Isomers | 99.1 | 91.4 | 79.7 | 73.2 | 85.9 |

TABLE XVII n-HEXANE ISOMERIZATION

Catalyzed by SrSnO3 on Spinel Treated Alumina
(S.A. = 106 m²/g)
Conditions: 148° C, 0 psig

| Time (Min.) | 5 | 58 | 104 | 147 | Avg. |
|---|---|---|---|---|---|
| Product (Wt. %) | | | | | |
| 2,3-dimethylbutane and 2-methylpentane | 0.49 | 0.48 | 0.48 | 0.46 | |
| 3-methylpentane | 0.48 | 0.48 | 0.49 | 0.48 | |
| Methylcyclopentane | 1.71 | 1.78 | 1.85 | 1.87 | |
| Cyclohexane | 0.15 | 0.23 | 0.25 | 0.24 | |
| n-hexane (feed) | 96.75 | 96.53 | 96.70 | 96.73 | |
| Other | | | | | |
| Wt. % Conversion | 3.25 | 3.47 | 3.30 | 3.27 | 3.32 |
| % Selectivity to C6 Isomers | 87.2 | 85.6 | 93.0 | 93.3 | 89.8 |

TABLE XVIII n-HEXANE ISOMERIZATION

Catalyzed by SrZrO3 (pure material, unsupported,
S.A. = 11 m²/g)
Conditions: 149° C, 0 psig

| Time (Min.) | 5 | 48 | 95 | 138 | 208 | Avg. |
|---|---|---|---|---|---|---|
| Product (Wt. %) | | | | | | |
| 2,3-dimethylbutane and 2-methylpentane | 0.49 | 0.47 | 0.45 | 0.44 | 0.43 | |
| 3-methylpentane | 0.51 | 0.49 | 0.48 | 0.47 | 0.46 | |
| Methylcyclopentane | 1.75 | 1.77 | 1.81 | 1.74 | 1.74 | |
| Cyclohexane | 0 | 0 | 0 | 0 | 0 | |
| n-hexne (feed) | 96.77 | 96.92 | 96.92 | 96.98 | 96.96 | |
| Other | 0.48 | 0.35 | 0.34 | 0.37 | 0.41 | |
| Wt. % Conversion | 3.23 | 3.08 | 3.08 | 3.02 | 3.04 | 3.09 |
| % Selectivity to C6 Isomers | 85.1 | 88.6 | 89.0 | 87.7 | 86.5 | 87.4 |

TABLE XIX

BENZENE HYDROGENATION TO HEXANE ISOMERS

Catalyzed by LaCrO3 on Spinel Treated Alumina
(Calcined at 600° C)
Conditions: 148° C, 0 psig

| Time (Min.) | 6 | 84 | 127 | 168 | 218 | 259 |
|---|---|---|---|---|---|---|
| Product (Wt. %) | | | | | | |
| 2,3-dimethylbutane and 2-methylpentane | 60.66 | 41.63 | 19.08 | 0 | 0 | 0 |
| n-hexane | 16.15 | 10.45 | 8.46 | 6.15 | 3.15 | 2.52 |
| Methylcyclopentane | 3.94 | 2.16 | 2.37 | 2.18 | 0.24 | 0.19 |
| Cyclohexane | 0 | 0.42 | 0.45 | 0.43 | 0.44 | 0 |
| Benzene (feed) | 17.81 | 44.33 | 67.35 | 91.24 | 93.98 | 97.29 |
| Other | 1.44 | 1.01 | 2.29 | 0 | 2.19 | 0 |
| Wt. % Conversion | 82.19 | 55.67 | 32.65 | 8.76 | 6.02 | 2.71 |
| % Selectivity to C6 Isomers | 98.2 | 98.2 | 93.0 | 100.0 | 63.6 | 100.0 |

TABLE XX

HYDROGENATION OF BENZENE TO C6 ISOMERS

Catalyzed by SrSnO3 on Spinel Treated Alumina
Conditions: 148° C, 0 psig

| Time (min.) | 6 | 52 | 147 | 190 | 268 | 306 |
|---|---|---|---|---|---|---|
| Product (Wt. %) | | | | | | |
| n-hexane | 0.90 | 0.68 | 0.82 | 0.71 | 0.72 | 0.61 |
| Methylcyclopentane | 0.10 | 0.10 | 0.14 | 0.11 | 0.12 | 0.09 |
| Benzene (feed) | 98.96 | 99.17 | 99.00 | 98.86 | 98.91 | 99.26 |
| Other | 0.04 | 0.05 | 0.04 | 0.32 | 0.25 | 0.04 |
| Wt. % Conversion | 1.04 | 0.83 | 1.00 | 1.14 | 1.09 | 0.74 |
| Selectivity to Saturated C6 Isomers | 96.2 | 94.0 | 96.0 | 71.9 | 77.1 | 94.6 |

TABLE XXI

HYDROGENATION OF BENZENE

Catalyzed by AgNbO3 Spinel Treated Alumina
Conditions: 148° C, 0 psig

| Time (Min.) | 139 | 180 | 221 | 263 |
|---|---|---|---|---|
| Product (Wt. %) | | | | |
| 2,3-dimethylbutane and 2-methylpentane | 62.51 | 35.30 | 9.53 | 0 |
| Normal hexane | 6.41 | 5.74 | 5.76 | 3.03 |
| Methylcyclopentane | 2.96 | 1.65 | 1.76 | 1.58 |
| Cyclohexane | 0 | 0.30 | 0.27 | 0.23 |
| Benzene | 28.09 | 57.01 | 82.68 | 95.17 |
| Other | 0.03 | 0 | 0 | 0 |
| Wt. % Conversion | 71.91 | 42.99 | 17.32 | 4.83 |
| % Selectivity to saturated C6 isomers | 100.0 | 100.0 | 100.0 | 100.0 |

The experiments summarized in Tables VI to XXI show that SrSnO3 which is a perovskite containing no transition metal was inactive for most of the hydrocarbon conversion reactions demonstrated in Tables VIII, XVII and XX.

As can be seen from the tests utilizing SrZrO3, incorporation of a transition metal, e.g. Zr, improved catalytic activity even though SrZrO3 is a bulk perovskite with low surface area (compare Table XVII and Table XVIII).

As can be seen from these experiments, the supported perovskites of the present invention catalyze a wide variety of hydrocarbon conversion reactions, such as dehydrogenation, as shown in Tables VI and VII; reforming (isomerization and dehydrogenation) as shown in Tables X and XI; selective cracking (loss of methyl group) as shown in Tables XII, XIII and XIV; isomerization as shown in Tables XV and XVI, and hydrogenation as shown in Tables XIX and XXI.

The $AgNbO_3$ on spinel treated alumina used in the tests of Table XIV, Table XV and Table XXI had a surface area of 96 $m^2/g$. The $CaThO_3$ on spinel treated alumina used in the tests of Table IX, Table XIII and Table XVI had a surface area of 68 $m^2/g$.

What is claimed is:

1. In a supported perovskite catalyst for hydrocarbon conversion and hydrocarbon treating processes which comprises a perovskite comprising at least one transition metal, the improvement which comprises: a support comprising a metal oxide and a spinel on the surface of said metal oxide, said spinel being selected from the group consisting of normal spinel and inverse spinel, said normal spinel having an empirical formula $MY_2O_4$ wherein M and Y in said normal spinel formula are cations of different metals and wherein one of said cations of said normal spinel formula is the metal of said metal oxide, said inverse spinel having an empirical formula $Y(XY)O_4$ wherein Y and X in said inverse spinel formula are cations of different metals, and wherein one of said cations of said inverse spinel formula is the metal of said metal oxide, said supported catalyst having a surface area of at least 65 $m^2/g$.

2. The supported perovskite catalyst of claim 1 wherein said metal oxide is a porous metal oxide.

3. The supported perovskite catalyst of claim 1 wherein said metal oxide is selected from the group consisting of $Al_2O_3$, MgO, $TiO_2$, $ZrO_2$, $HfO_2$, $WO_3$ and mixtures thereof.

4. The supported catalyst of claim 1 wherein said metal oxide is alumina.

5. The supported perovskite catalyst of claim 1 wherein said perovskite is an oxide of at least two metals and wherein the sum of the ionic charges of the metals of the oxide equals six.

6. The supported perovskite catalyst of claim 1 wherein said perovskite is selected from the group consisting of $LaCoO_3$, $LaCrO_3$, $CaThO_3$, $AgNbO_3$ and $SrZrO_3$.

7. The supported perovskite catalyst of claim 1 wherein the surface area of the supported catalyst ranges from about 65 $m^2/g$ to about 250 $m^2/g$.

8. The supported perovskite catalyst of claim 1 wherein the cations of said spinel are selected from the group consisting of Al, Mg, Fe, Co, Ni, Mn, Zn, Ti, Sn, Cu and Cr.

9. The catalyst of claim 1 wherein said metal oxide is alumina and wherein said spinel is $MgAl_2O_4$.

10. A supported perovskite catalyst which comprises a perovskite selected from the group consisting of $LaCoO_3$, $LaCrO_3$, $CaThO_3$, $AgNbO_3$ and $SrZrO_3$, said perovskite being composited with a support comprising alumina and a spinel on the surface of said alumina, said spinel being $MgAl_2O_4$.

11. A process for the preparation of a supported perovskite catalyst for hydrocarbon conversion and hydrocarbon treating processes, which comprises:

a. treating a metal oxide having an initial surface area ranging from about 50 to about 250 $m^2/g$ with at least one metal component such that the algebraic sum of the ionic charges of the metal of said metal oxide and the metal of said metal component corresponds to the algebraic sum of cations required for spinel formation, said spinel being selected from the group consisting of normal spinel and inverse spinel, said normal spinel having an empirical formula $MY_2O_4$, wherein M and Y in said normal spinel formula are cations of different metals, said inverse spinel having an empirical formula $Y(XY)O_4$, wherein Y and X in said inverse spinel formula are cations of different metals;

b. calcining the treated metal oxide resulting from step (a) at a temperature sufficient to produce a spinel on at least a portion of the surface of said treated metal oxide;

c. treating the calcined metal oxide having said surface spinel thereon resulting from step (b) with perovskite precursor metal components comprising at least one transition metal component;

d. calcining at a temperature of at least 540° C. the perovskite precursor treated-material resulting from step (c) to convert said perovskite precursors to a perovskite and thereby produce a supported perovskite catalyst.

12. The process of claim 11 wherein said oxide is a porous inorganic metal oxide or a porous inorganic metal oxide gel.

13. The process of claim 11 wherein said metal oxide is selected from the group consisting of $Al_2O_3$; MgO; $TiO_2$, $ZrO_2$; $HfO_2$; $WO_3$ and mixtures thereof.

14. The process of claim 11 wherein said metal oxide comprises alumina.

15. The process of claim 11 wherein said perovskite precursor metal components are selected from components having cationic charges such that the algebraic sum of said cations equals six.

16. The process of claim 11 wherein said perovskite precursor metal components are two metal components, the sum of the cationic charges of which equals six.

17. The process of claim 11 wherein said perovskite precursor metal components are selected from the group consisting of metals, metal oxides, metal hydroxides, metal salts and mixtures thereof of metals having a valence ranging from 1 to 5.

18. The process of claim 11 wherein said perovskite of step (d) is an oxide of two or more metals, the sum of the ionic charges of which equals six.

19. The process of claim 11 wherein additional catalytic active metal components are composited with said supported perovskite catalyst.

20. A process for the preparation of a supported $LaCoO_3$ persovkite catalyst which comprises:

a. impregnating a gamma alumina gel having a surface area of about 185 $m^2/g$ with $Mg(NO_2)_2$;

b. calcining the impregnated alumina alumina gel at a temperature of about 540° C., thereby producing a surface coating of $MgAl_2O_4$ spinel on said gamma alumina;

c. impregnating the spinel-coated alumina resulting from step (b) with an equimolar solution of $La(NO_3)_3.6H_2O$ and $Co(NO_3)_2.6H_2O$;

d. calcining at a temperature of at least 540° C. the impregnated material resulting from step (c) and e. recovering a supported $LaCoO_3$ catalyst.

21. The process of claim 20 wherein said supported $LaCoO_3$ catalyst has a surface area of at least about 65 $m^2/g$.

22. The process of claim 11 wherein said metal oxide resulting from step (a) is calcined at a temperature ranging from about 500° C to about 1000° C. to produce said spinel.

* * * * *